United States Patent [19]
Wonderley et al.

[11] Patent Number: 5,299,357
[45] Date of Patent: Apr. 5, 1994

[54] DISPOSABLE SURGICAL SCALPEL WITH SAFETY GUARD

[75] Inventors: Jeff W. Wonderley, Ft. Defiance; Donald G. Strickland, Charlottesville, both of Va.

[73] Assignee: American Safety Razor Company, Verona, Va.

[21] Appl. No.: 808,891

[22] Filed: Dec. 18, 1991

[51] Int. Cl.⁵ .................. B26B 1/00; B26B 1/04; B26B 3/00
[52] U.S. Cl. .................. 30/339; 30/335; 30/329; 30/320
[58] Field of Search .......... 30/320, 329, 332, 333, 30/334, 335, 339, 151, 156, 157, 160, 161; 606/167, 172, 181

[56] References Cited

U.S. PATENT DOCUMENTS

| | | | |
|---|---|---|---|
| 2,304,332 | 12/1942 | Bodkin | 30/335 |
| 3,412,467 | 11/1968 | Matwijcow | 30/335 |
| 3,889,368 | 6/1975 | Himeno | 30/335 |
| 3,905,101 | 9/1975 | Shepherd | 30/339 |
| 3,906,626 | 9/1975 | Riuli | 30/320 |
| 4,523,379 | 6/1985 | Osterhout et al. | 30/151 |
| 4,576,164 | 3/1986 | Richeson | 128/305 |
| 4,719,915 | 1/1988 | Porat et al. | 128/305 |
| 4,735,202 | 4/1988 | Williams | 128/305 |
| 4,768,509 | 9/1988 | Grosvenor et al. | 30/335 |
| 4,803,751 | 2/1989 | Cousins | 15/236 |
| 4,958,625 | 9/1990 | Bates et al. | 606/167 |
| 4,985,034 | 1/1991 | Lipton | 606/167 |
| 5,071,426 | 12/1991 | Dolgin et al. | 30/335 |

*Primary Examiner*—Richard K. Seidel
*Assistant Examiner*—Paul M. Heyrana
*Attorney, Agent, or Firm*—Willian Brinks Olds Hofer Gilson & Lione

[57] ABSTRACT

The scalpel includes a handle mounting a scalpel blade at one end and having a slot opening through and between its opposite sides. A guard, including two side members straddling the handle, is mounted for sliding movement between a protective position overlying the blade and a retracted position exposing the blade for use. The side members are connected by an element extending through the handle slot and one or more resilient fingers in the slot cooperates with the element to detent the guard in one of the positions. In a further form, the guard is slidable into a permanently locked position relative to the handle, thereby preventing reuse of the scalpel and inadvertent exposure of the blade.

58 Claims, 7 Drawing Sheets

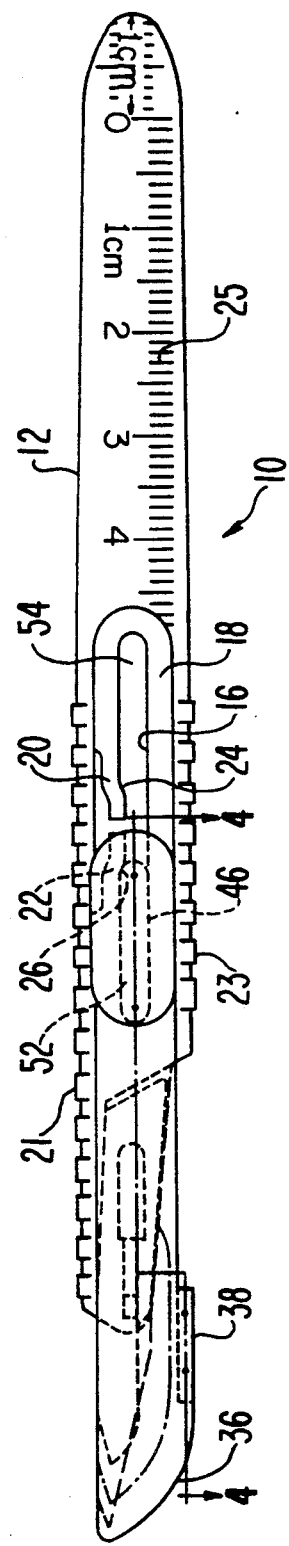
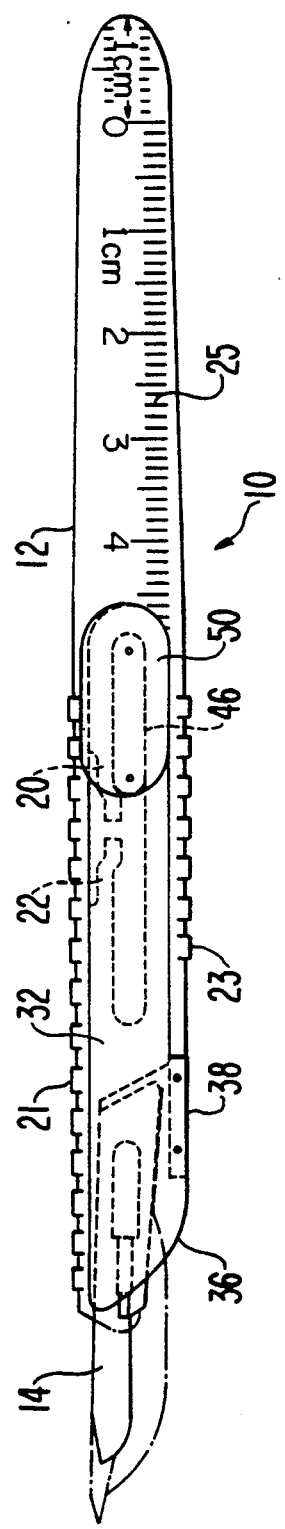

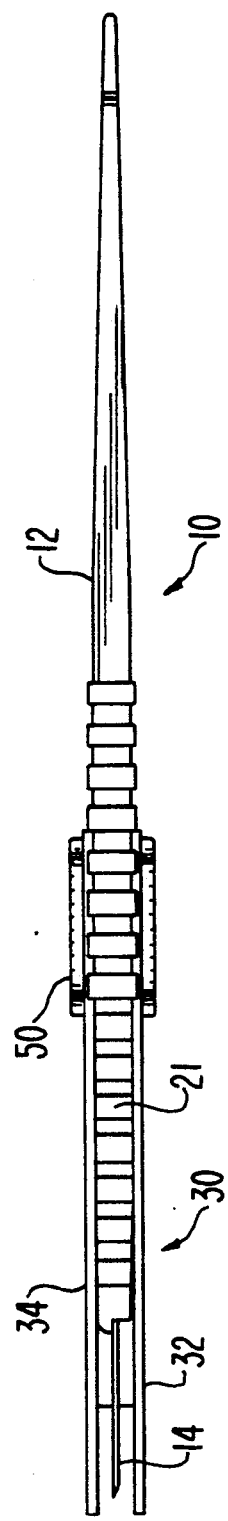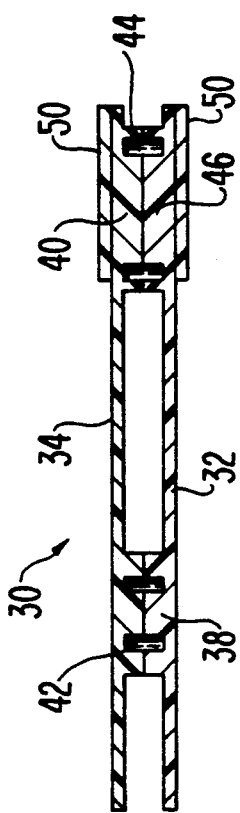

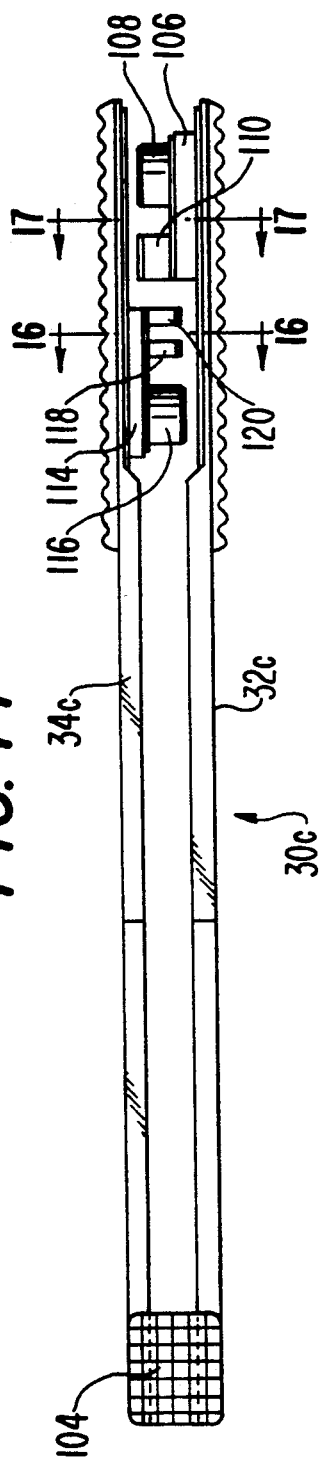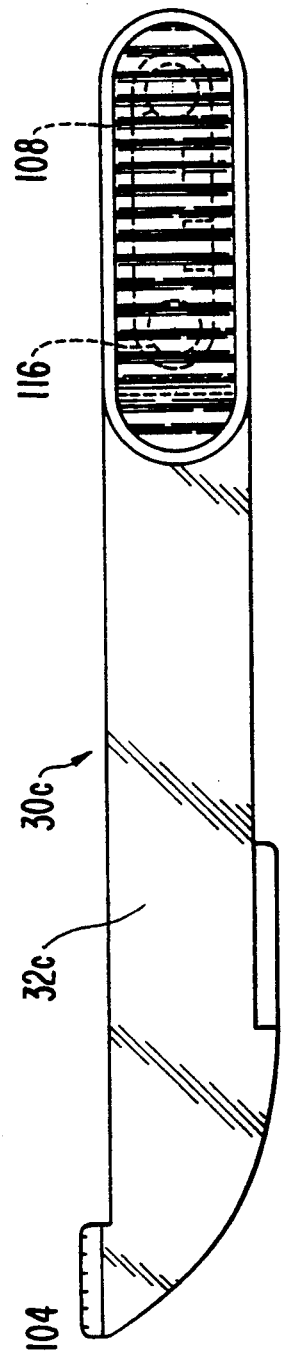

DISPOSABLE SURGICAL SCALPEL WITH SAFETY GUARD

BACKGROUND AND SUMMARY OF THE INVENTION

The present invention relates to a surgical scalpel and particularly relates to a surgical scalpel having a guard movable along the scalpel handle and blade between a protective position temporarily overlying and covering the scalpel blade and a retracted position exposing the blade for use. The invention also relates to a scalpel wherein the guard may additionally be moved into a permanent protective position permanently covering and overlying the blade.

Disposable surgical scalpels are well known in the art and often comprise a handle, typically formed of a plastic material, to which is attached either permanently or detachably, a scalpel blade. Such disposable surgical scalpels are conventionally packaged in sterile containers, e.g., flexible plastic packages or pouches. Once removed from the container, the scalpel blade is typically exposed for use. This, of course, also exposes the blade to all individuals, doctors, nurses, medical technicians, etc., associated with a surgical procedure, as well as those individuals charged with the disposal of the used scalpel. Thus, even with the exercise of great care, individuals are frequently inadvertently cut by the exposed scalpel blade. The dangers of being cut and transmission of infectious diseases when cut by a used scalpel blade are thus ever-present. Even when using scalpels having blades which are detached after use and disposed in a sharps container, those individuals handling the scalpels, blades or sharps containers remain at risk.

Surgical scalpels having sheaths affording individuals protection against being cut by exposed blades are known in the prior art. For example, in U.S. Pat. No. 3,906,626, there is disclosed a sheath for a surgical scalpel which is movable between a retracted position, exposing the blade for use, and an extended position, substantially wholly enclosing the blade. This scalpel also provides a sheath movable into a third and permanently locked position overlying the blade, whereby the blade cannot be reused and individuals, including those charged with the disposal of the blade, are protected from being cut by the blade. This scalpel, however, has many drawbacks. The blade lacks stability in the hands of the surgeon because the sheath completely overlies the handle in the retracted position of the sheath which corresponds to the use position of the scalpel. That is, the surgeon must grasp the sheath, not the handle, in order to use the scalpel. There is accordingly a danger of play between the sheath and the handle when the scalpel is used by the surgeon. Further, two hands are necessary to displace this sheath between a position exposing the blade for use and its protective position. These and other disadvantages of the scalpel disclosed in that patent will become apparent from reference to the following description of the present invention.

According to the present invention, there is provided a novel and improved disposable scalpel including a handle having a scalpel blade permanently secured adjacent one end of the handle and projecting therefrom, and a guard movable between positions exposing the scalpel blade for use, and a protective position temporarily covering the blade. In a further embodiment, the guard is also movable into a protective position permanently covering the blade. The scalpel handle also includes a slot opening through and between the opposite sides of the handle to facilitate sliding movement of the guard along the handle and latching or detenting of the guard in its various positions along the handle. In accordance with one form of the present invention, the guard comprises a pair of side guard members overlying opposite sides of, i.e., straddling, the handle and connected one to the other by an element passing through the slot in the handle. The side guard members are also connected one to the other adjacent the lower sides of their opposite ends to maintain the side members in predetermined spaced relation to one another. This latter connection prevents the side members from spreading apart and entry of a human digit between the side members in the area of the scalpel blade. Importantly, the upper or top edge of the guard is completely open between the two side members, exposing the upper edge of the handle and enabling it to project above the upper edges of the side members. In this manner, the upper edge of the handle may be engaged by one or more of the surgeon's fingers whereby direct finger control of the scalpel handle and blade during use is provided and without interference from the guard. It will also be appreciated from the ensuing description and the drawing figures that the element passing through the slot is shaped for cooperation with the margins of the slot to maintain the guard in positions straddling the handle in all positions of the guard along the handle. That is, the element and slot cooperate to prevent the guard from pivoting in the plane of the handle.

The guard is also detented in each of its positions by a unique cooperation of the element connecting the side members of the guard one to the other in the slot and one or more detenting or locking members formed within the slot of the handle. In this first embodiment of the invention, the guard is movable between a protective position overlying the blade and a retracted position exposing the blade for use. Thus, in this first embodiment and when the guard is in its protective position covering the blade, the forward edge of the element is engaged against the forward end wall of the slot. A spring biased finger engages the rear edge of the element to maintain the guard in its protective position. By displacing the guard rearwardly to expose the blade for use, the element displaces the finger out of the way, enabling the guard to be located in its retracted position with the rear edge of the element engaging against the rear end wall of the slot. In that position, a second finger engages the forward edge of the element, maintaining the guard in the retracted position. The guard can thus be moved between the retracted position and its protective position simply by sliding the guard in opposite directions along the handle, the fingers being cammed out of the way of and by the element during the sliding movement. The element and hence the guard is detented by the respective fingers in each of the protective and retracted positions.

In a second embodiment hereof, a single finger formed within the slot cooperates with the element to maintain the guard detented in each of its retracted and temporary positions as well as in a permanent protective position. In its temporary protective position, the finger has a cam follower surface engaging the rear edge of the element to prevent rearward sliding movement of the guard relative to the handle. A smaller finger along the opposite side of the slot adjacent its forward end engages the forward edge of the element to prevent the guard from sliding forwardly from its temporary protective position into its forwardmost permanent protective position. The guard is slidable rearwardly into its retracted position by sliding the element along the slot and biasing the first-mentioned finger outwardly. When the element engages the rear end of the slot, a second cam follower surface on the first finger engages the forward edge of the slot to detent the guard in its retracted position.

To move the guard into its permanent locking position, the guard is moved forwardly past its temporary protective position and against the bias of the small finger at the forward end of the slot into its permanent locking protective position. The first finger resiliently bears against the element during its forward sliding movement until the guard reaches its permanently locked position. At that time, the first finger is biased into the slot and into the rearward path of movement of the element, thereby locking the guard in its forwardmost permanent protective position. These locking means, including the first finger and the small forward finger, lie wholly within the confines of the slot of the handle. Thus, no lateral or transverse movement is required to move the guard or detent it in its protective or retracted positions.

In a third embodiment hereof, a pair of forwardmost finger locks, rear finger detents forwardly extending locking fingers are provided in the slot and, in conjunction with the previously described small forward finger, maintain the guard in the retracted, temporary protective and permanently locked positions. This form is used where large scalpel blades are necessary, hence a longer slot.

The final disclosed embodiment of the present scalpel includes a one-piece molded guard having side members, each of which has a pin for projecting inwardly within the slot in the scalpel handle. One side member also includes adjacent its pin a pair of inwardly projecting latching detents, while the opposite side member adjacent its pin includes a single inwardly projecting latching detent. The handle slot in this embodiment has a longitudinally extending central rib defining a pair of tracks along its opposite sides. A raised catch or projection extends along one of the tracks. In this form, the pins and latching detents of the side members are inserted into the opposite sides of the handle slot with the latching detents engaging on opposite sides of the central rib and the handle. The latching detents therefore maintain the side members along opposite sides of the handle, preventing their lateral outward movement away from one another and the handle. The pins also engage between the opposite sides of the handle slot, including the central rib for guiding the guard along the handle and preventing pivotal movement of the guard relative to the handle in the plane of the handle.

In this form, the guard is similarly movable between a retracted use position for the scalpel, a temporary protective position and a permanent locked position overlying the scalpel blade. To accomplish this, inwardly depending fingers are disposed at opposite ends of the slot for engaging over the pins. Thus, in the retracted position of the guard, the pin on one of the side members is located in the end of the slot past the finger, which retains the guard in the retracted position. When the guard is moved forwardly along the slot, the forwardmost pin engages beyond the forwardmost finger and the forwardmost latching detent engages the catch along the handle track, temporarily preventing further movement of the guard in the forward direction relative to the handle. The pin of the opposite side member prevents rearward movement of the guard relative to the handle. To locate the guard in a permanent protective position relative to the scalpel blade, the guard is pushed forwardly from the temporary position into the permanent position, with the first latching detent riding over the catch whereby the catch is disposed between the pair of latching detents on the one side member, preventing movement of the guard in either longitudinal direction. Note in this embodiment that the latching detents of each side member maintain the side members closely adjacent the handle.

The scalpel of the present invention affords various additional advantages and features in comparison with conventional scalpels including those with protective sheaths. For example, the upper edge of the handle of the scalpel blade, as discussed previously, is fully exposed in all positions of the guard so that control of the cutting edge by the surgeon may be maintained by direct finger contact with the scalpel handle during use. The elongation of the element, in one embodiment, and the pins of the still further embodiment described above, each projecting into the slot, prevents the guard from pivoting in the plane of the handle from the positions straddling the handle and blade. Moreover, the guard is slidable along the handle between all positions using only one hand. It does not require two hands to move the guard between its protective and retracted positions. Further, the guard is slidable between retracted and temporary protective positions multiple times, whereby the scalpel may be used, set aside with the guard in its temporary protective position, and then reused with the guard movable again into its retracted position. Still further, the construction of the handle and guard may be of all plastic material whereby the scalpel may be formed and assembled inexpensively. In the first embodiment, the guard is a two-piece molded construction, while in the last embodiment described above, the guard may be of a one-piece molded construction.

In a preferred embodiment according to the present invention, there is provided a surgical scalpel blade, comprising an elongated scalpel handle having a slot opening through and between opposite sides of the handle, a scalpel blade carried by the handle adjacent one end thereof and a guard carried by the handle for sliding movement relative to the handle between a protective position covering the blade and a retracted position exposing the blade for use. The guard includes side members overlying opposite sides of the handle, respectively, and has an element connecting the side members one to the other and disposed in the slot. The element is movable along the slot in response to sliding movement of the guard relative to the handle between the protective and retracted positions. A locking member is carried by the handle in the slot for engaging the element in the protective position of the guard relative to the handle for releasably maintaining the guard in the protective position thereof and movable to enable the guard to move from the protective position toward the retracted position. Means are carried by the handle and cooperable with the element in the retracted position of the guard to releasably maintain the guard in the retracted position relative to the handle.

In a further preferred embodiment according to the present invention, there is provided a surgical scalpel blade, comprising an elongated scalpel handle having a slot opening through and between opposite sides of the handle, a scalpel blade carried by the handle adjacent one end thereof, a guard carried by the handle for sliding movement relative to the handle in a first direction from a temporary protective position covering the blade into a retracted position exposing the blade for use and in a second direction opposite the first direction from the temporary protective position into a permanent protective position covering the blade. The guard includes an element disposed in the slot and movable therealong in response to sliding movement of the guard relative to the handle in the first and second directions. A locking member is carried by the handle in the slot for engaging and releasably detenting the element in the temporary protective position of the guard relative to the handle and movable to enable the guard to move in the first direction from the temporary protective position toward the retracted position and in the second direction into the temporary protective position. The locking member is movable to engage the element in the permanent protective position to prevent movement of the guard relative to the handle in the first direction thereby to permanently lock the guard in the permanent protective position.

In a further preferred embodiment according to the present invention, there is provided a surgical scalpel blade, comprising an elongated scalpel handle having elongated top and bottom edges and guide surfaces, a scalpel blade carried by the handle adjacent one end thereof and a guard carried by the handle for sliding movement relative to the handle between a protective position covering the blade and a retracted position exposing the blade for use. The guard has an element engageable with the guide surfaces of the handle and movable along the handle in response to sliding movement of the guard relative to the handle between the protective and retracted positions and has discrete side members unconnected one to the other along at least one of the top and bottom edges of the handle, leaving one edge free for engagement by a finger of a user of the scalpel. A locking member is carried by the handle for engaging the element in the protective position of the guard relative to the handle for releasably maintaining the guard in the protective position thereof and movable to enable the guard to move from the protective position toward the retracted position and means are carried by the handle and cooperable with the element in the retracted position of the guard to releasably maintain the guard in the retracted position relative to the handle.

In a further preferred embodiment according to the present invention, there is provided a surgical scalpel blade, comprising an elongated scalpel handle having a slot opening through and between opposite sides of the handle, a scalpel blade carried by the handle adjacent one end thereof and a guard carried by the handle for sliding movement relative to the handle between a protective position covering the blade and a retracted position exposing the blade for use. The guard includes side members overlying the opposite sides of the handle, respectively, with the guard carrying locking means disposed in the slot and movable along the slot in response to sliding movement of the guard relative to the handle. A locking member is carried by the handle in the slot for engaging the locking means in the protective position of the guard relative to the handle for releasably locking the guard in the protective position thereof and movable to enable the guard to move from the protective position toward the retracted position. Means are carried by the handle and cooperable with the locking means in the retracted position of the guard to releasably maintain the guard in the retracted position relative to the handle.

In a further preferred embodiment according to the present invention, there is provided a surgical scalpel blade, comprising an elongated scalpel handle having a slot opening through and between opposite sides of the handle, a scalpel blade carried by the handle adjacent one end thereof and a guard carried by the handle for sliding movement relative to the handle between a protective position covering the blade and a retracted position exposing the blade for use. The guard includes side members overlying the opposite sides of the handle, respectively, each side member including a guide projecting inwardly therefrom into the slot for guiding the guard and the handle relative to one another in response to sliding movement of the guard relative to the handle between the protective and retracted positions, the guides being disposed at longitudinally spaced positions relative to one another along the slot. A pair of longitudinally spaced locking fingers are carried by the handle in the slot for engaging the guides, respectively, in the protective and retracted positions of the guard relative to the handle, one of the locking fingers being engageable with one of the guides to releasably maintain the guard in the protective position thereof, the other of the locking fingers being engageable with the other of the guides to releasably maintain the guard in the retracted position relative to the handle. Means are provided extending into the slot from each of the side members and are engageable with the handle for preventing displacement of the side members laterally outwardly in a direction away from the handle.

Accordingly, it is a primary object of the present invention to provide a novel and improved disposable scalpel with a guard movable between a retracted position exposing the scalpel blade for use, and a temporary protective position overlying and covering the blade, protecting individuals from the blade, and, in another form, a permanent protective position overlying and covering the blade whereby the guard cannot be removed from its permanent protective position without effectively destroying the scalpel per se or the guard.

These and further objects and advantages of the present invention will become more apparent upon reference to the following specification, appended claims and drawings.

BRIEF DESCRIPTION OF THE DRAWING FIGURES

FIG. 1 is a side elevational view of a disposable scalpel with guard constructed in accordance with the present invention and illustrating the guard in a temporary protective position overlying the blade;

FIG. 2 is a view similar to FIG. 1 illustrating the guard in a retracted position exposing the blade for use;

FIG. 3 is a top plan view of the scalpel illustrated in FIG. 1;

FIG. 4 is a cross-sectional view of the guard for the scalpel of FIG. 1;

FIG. 14 is an enlarged top plan view of a guard for use in the embodiment illustrated in FIG. 11;

FIG. 15 is a side elevational view of the guard illustrated in FIG. 14;

DETAILED DESCRIPTION OF THE DRAWING FIGURES

Figure 5:
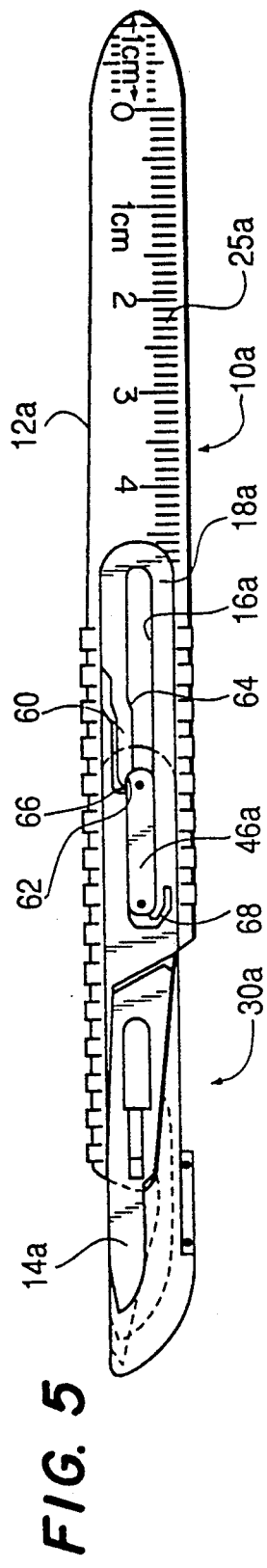
FIGS. 5, 6 and 7 are respective side elevational views of a second embodiment of the present invention with one side member of the guard removed and illustrating the guard in a temporary protective position, a retracted position exposing the blade for use, and a permanent protective position, respectively.

Reference will now be made in detail to a present preferred embodiment of the invention, an example of which is illustrated in the accompanying drawings.

Referring now to FIG. 1, there is illustrated a scalpel constructed in accordance with the present invention and generally designated 10. Scalpel 10 includes a scalpel handle 12 and a blade 14, preferably permanently secured at one end of handle 12, for example, by staking. It will be appreciated that various sizes of blades 14 may be permanently or releasably attached to handle 12, depending on the nature of the use of the scalpel and variously sized blades are illustrated by the dashed lines. The handle 12 is preferably formed entirely of a plastic material and, in this form, includes a central slot 16 extending through and between the opposite sides of handle 12. Slot 16 is defined by a laterally recessed rim 18 which extends about and forms the margin of slot 16, the rim 18 opening forwardly toward the blade. In this embodiment, rim 18 has a pair of longitudinally oppositely facing fingers 20 and 22 spaced inwardly from one edge of slot 16 to define cam surface followers or detents 24 and 26, respectively, facing in opposite directions. The fingers 20 and 22 terminate short of one another and are independently and resiliently movable away from their illustrated positions in slot 16.

Handle 12 also includes a plurality of ribs 21 longitudinally spaced one from the other along the upper edge of the handle and along the forward position thereof. Similar ribs 23 are disposed along the lower edge of the handle 12. The ribs 21 and 23 facilitate gripping the scalpel by the surgeon during use. As discussed hereinafter, these ribs are exposed in all positions of the scalpel's guard. Also provided along one, and preferably both side faces of the handle, is dimensional indicia, indicated by 25, in this case given in centimeters.

Referring now particularly to FIGS. 3 and 4, scalpel 10 includes a guard, generally designated 30, comprising a pair of elongated side members 32 and 34. Side members 32 and 34 are mirror-images of one another.

Each side member includes an elongated side having an arcuately shaped forward end edge 36 and an inwardly extending flange 38 along the lower side of guard 30 adjacent its forward end. Each side member also includes an inwardly extending flange 40 substantially medially between the upper and lower edges of the guard and adjacent its rear end portion. Flanges 38 and 40 of each side member are connected to the corresponding flanges 38 and 40 of the opposite side member by pins 42 and 44, respectively, as illustrated in FIG. 4.

The connected flanges 40 form an element 46 elongated in the longitudinal direction of the handle. Element 46 is disposed in slot 16 in the handle. The connected flanges 38 adjacent the forward end of guard 30 underlie, respectively, the edge of the blade in the protective position of the guard and the lower edge of the handle in the retracted position of the guard. For reasons discussed hereinafter, the upper edge of the side members 32 and 34 of the guard are unconnected. In its assembly with the handle, the upper and lower edges of the handle including ribs 21 and 23, respectively, thus extend through the guard, as illustrated in FIGS. 1 and 2. Guard 30 also includes a pair of side grips 50 formed along the rear end portion of the guard. The outer faces of grips 50 may be serrated or otherwise formed to provide a frictional contact surface readily and easily gripped between an individual's fingers for sliding guard 30 between and into its various positions along handle 12. Rear portions of side members 32 and 34 extend along the opposite sides of the handle within rim 18. It is significant that the side members 32 and 34 engage rim 18 and that element 46 is elongated in the slot 16 such that any torquing action on the guard tending to pivot the forward end of the guard away from the blade is forcefully resisted by the engagement of the side members against rim 18 and by the cooperation of elongated element 46 lying in a corresponding elongated portion of slot 16.

With the guard assembled to the handle as described, the guard is movable between a temporary protective position covering and overlying the blade 14 as illustrated in FIG. 1 and a retracted position exposing the blade for use, as illustrated in FIG. 2, it being appreciated that the guard is detented in both positions for temporarily fixing the guard in the selected position. As illustrated in FIG. 1, slot 16 has a forward slot portion 52 defined by the forward end of slot 16 and the inside edge of finger 22 which defines cam follower 26. Thus, cam follower 26 engages the rear trailing edge of element 46 when the guard lies in its protective position forwardmost in slot 16, as illustrated in FIG. 1. The resilient nature of finger 22 enables the guard to be detented in its protective position yet enables the guard for sliding movement from the protective position to the retracted position illustrated in FIG. 2. Thus, when an individual grasps the scalpel handle in the palm of his hand and places his thumb and index finger on the grips 50, the guard may be displaced rearwardly from its protective position against the bias of finger 22 and into the retracted position illustrated in FIG. 2. The rear finger 20 is cammed out of the way by element 46 as element 46 passes rearwardly along slot 16 such that element 46 may be disposed in the rear slot portion 54. In that position, finger 20 spring returns to the illustrated position to engage cam follower surface 24 against the leading edge of element 46, detenting the guard in the retracted position.

Similarly, by holding the handle in the palm of the individual's hand and placing the thumb and index fingers along grips 50, guard 30 may be advanced from the retracted position of FIG. 2 into the protective position illustrated in FIG. 1. In transitioning between the two positions, it will be appreciated that fingers 20 and 22 are resiliently displaced out of the way to enable the element 46 to pass along slot 16 between those positions. It is significant that the guard may be disposed in either position with only one hand, thus freeing the other hand for other work. Also, note that ribs 21 and 23 along upper and lower edges of the handle 12 are at all times exposed for gripping by the surgeon in both retracted and protective positions of the guard.

Figure 6:
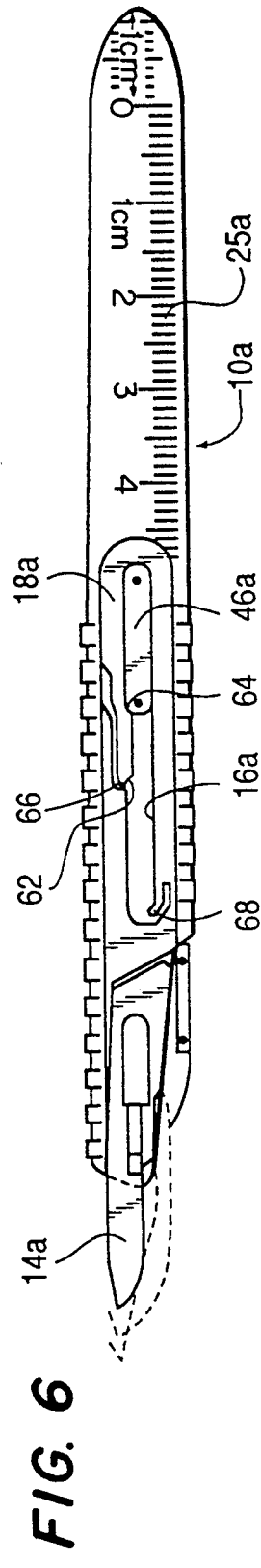
Figure 7:
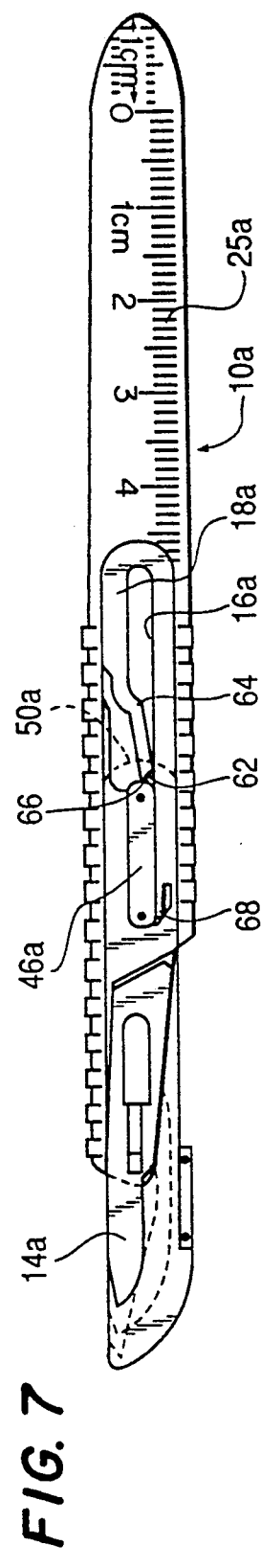

Referring now to the embodiment hereof illustrated in FIGS. 5-7, wherein like reference numerals refer to like parts, followed by the letter suffix "a", there is provided a scalpel 10a having a handle 12a, a blade 14a permanently or releasably attached to the handle 12a, and a guard 30a. In this form, however, the guard is movable between a temporary protective position covering the blade illustrated in FIG. 5, a retracted position exposing the blade for use illustrated in FIG. 6, and a permanently locked position covering the blade illustrated in FIG. 7. By permanent locking position is meant a position of the guard relative to the handle where the guard cannot be retracted or displaced from its permanent locked position without destroying either the guard, handle, or both.

In this form, slot 16a includes a laterally recessed rib 18a, the rib 18a forming within slot 16a a single finger 60. As illustrated in FIG. 5, finger 60 projects forwardly and is spaced from the corresponding upper edge of slot 16a. Finger 60 includes a pair of arcuate cam follower surfaces 62 and 64 along its underside but spaced longitudinally one from the other. Finger 60 also includes a tip 66. The lower portion of finger 60 between surfaces 62 and 64 thus projects into slot 16a as illustrated in FIG. 5. Finger 60, however, is biased for movement into the path of movement of element 46a, as illustrated in FIG. 7 and is resiliently movable out of the way as discussed hereinafter. Additionally, at the forward end of slot 16a, there is provided along its lower side an upwardly projecting finger 68 spaced from the forward end wall of slot 16a.

In using this embodiment of the scalpel, the scalpel 10a would typically be provided in a sterile package with the guard 30a in the temporary protective position illustrated in FIG. 5. In that position, element 46a is disposed in a forward portion of slot 16a, bounded at its forward edge by its engagement with finger 68, which prevents further forward movement of the guard relative to the handle, and at its rear edge by engagement with the arcuate surface 62 of finger 60. The engagement between the arcuate surface 62 and the trailing edge of element 46a in the temporary protective position of the guard 30a relative to handle 12a prevents finger 60 from assuming its normal position in slot 16a, as illustrated in FIG. 7. To displace guard 30a rearwardly from the temporary protective position of FIG. 5 to its retracted position, exposing the blade 14a for use illustrated in FIG. 6, handle 12a is disposed in the user's hand and grips 50a are grasped between the thumb and index finger, whereby the guard may be moved rearwardly. Upon moving the guard rearwardly, element 46a cams finger 60 upwardly out of the way of element 46a, enabling the guard to slide rearwardly into abutment against the rear end of slot 16a. In that position, as illustrated in FIG. 6, finger 60 resiliently moves toward its normal position illustrated in FIG. 7 to engage cam follower 64 against the edge of element 46a, thereby detenting guard 30a in the retracted position.

To displace guard 30a back into its temporary protective position, the user grasps grips 50a and slides guard 30a forwardly against the bias of finger 60. Finger 60 is thus displaced out of the path of travel of element 46a until the guard is advanced sufficiently such that the leading edge of element 46a engages finger 68. At that time, finger 60 springs back such that cam follower 62 engages the trailing edge of element 46a whereby the guard is detented between fingers 60 and 68 and maintained in the temporary protective position illustrated in FIG. 5.

After use and when it is desirable to dispose of the scalpel, the guard may be advanced into its permanently locked position illustrated in FIG. 7. To accomplish this, the handle is once again disposed in the user's hand and the grips grasped between the thumb and forefinger to advance the guard forwardly. By advancing the guard forwardly, the element 46a displaces finger 68 out of the way until the leading edge of element 46a engages the forward end of slot 16a. At that time, the trailing edge of element 46a is located forwardly of finger 60, enabling finger 60 to spring into its normal position illustrated in FIG. 7, engaging the trailing edge of element 46a and blocking rearward return movement of guard 30a from its permanent protective position. Consequently, the guard is permanently locked, covering the blade, whereby individuals are protected from inadvertent, casual and non-intentional contact with the blade. The scalpel may then be handled for further disposal without the danger attendant to an exposed blade.

Figure 8:
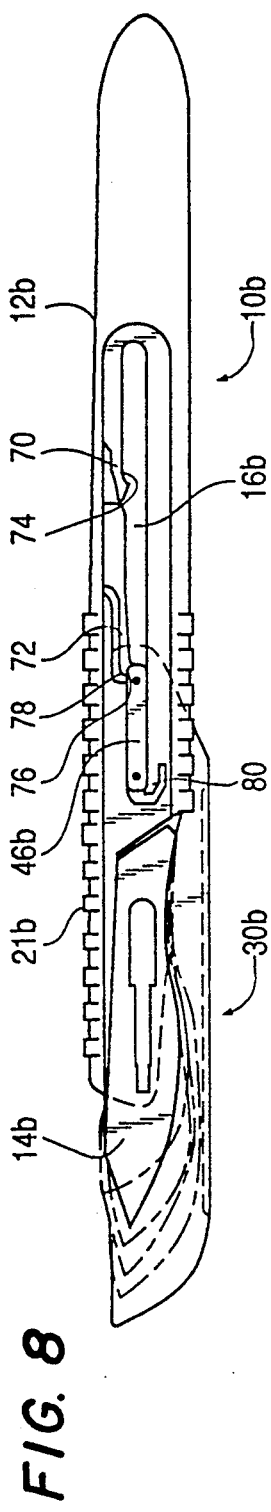
FIG. 8, 9 and 10 are views similar to FIGS. 5, 6 and 7, respectively, illustrating a further embodiment of a scalpel according to this invention.
Figure 9:
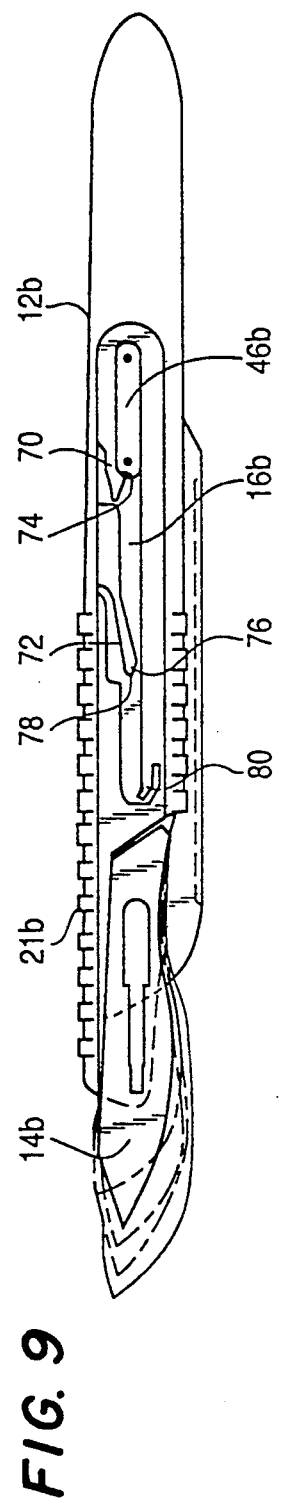
Figure 10:
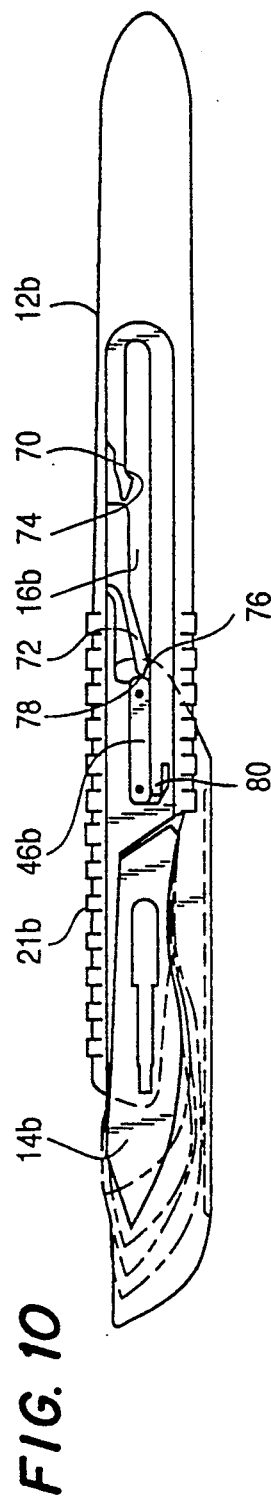

Referring to the embodiment hereof illustrated in FIGS. 8-10, like reference numerals are applied to like parts as in the prior embodiments, followed by the suffix "b". In this form, the scalpel carries substantially larger blades than disclosed in the prior embodiments and, accordingly, the range of travel of the guard relative to the handle and blade is increased. To accommodate that increase in range of travel, slot 16b is provided with a pair of forwardly extending fingers 70 and 72, respectively. Finger 70 is located adjacent the rear portion of slot 16b and has an arcuate cam follower surface 74 for engaging the leading edge of element 46b when the guard is moved to its retracted position, as illustrated in FIG. 9. Finger 72 is formed to normally project into slot 16b, as illustrated in FIG. 10, and includes an arcuate cam follower surface 76 along the underside of its forward edge. Finger 72 also includes a tip 78. Additionally, slot 16b includes at its forward end a finger 80 which projects upwardly into slot 16b, defining the forwardmost position of the element 46b when disposed in the temporary protective position.

In using this form of the invention, scalpel 10b would typically be provided in a sterile package with guard 30b covering blade 14b in its temporary protective position. Thus, element 46b is detented between the upwardly projecting finger 80 and the cam follower 76 of finger 72. Note that the engagement of cam follower 76 and element 46b prevents finger 72 from moving into its normal position within slot 16b as illustrated in FIGS. 9 and 10. To use scalpel 10b, grips 50b are grasped between the thumb and forefinger and the guard retracted along slot 16b. This retracting movement cams finger 72 out of the way of movement of element 46b and also cams finger 70 outwardly such that element 46b may be disposed in its rearmost position with its trailing edge against the rear end of slot 16b. In that position, the forward edge of the element 46b is engaged by the arcuate cam follower surface 74 of finger 70 whereby element 46b and hence guard 30b is detented in the retracted position.

After use, guard 30b may be displaced forwardly into its temporary protective position illustrated in FIG. 8. In displacing guard 30b forwardly, fingers 70 and 72 are displaced upwardly out of the way of movement of element 46b until the leading edge of element 46b engages finger 80. In that position, it will be appreciated from a review of FIG. 8 that the element 46b and hence guard 30b is detented between finger 80 and the arcuate cam follower surface 76 of finger 72 whereby the guard 30b is releasably maintained in the temporary protective position. It will be appreciated that the guard may be displaced rearwardly and forwardly multiple times between the retracted and temporary protective positions.

When the scalpel is to be discarded, the guard is advanced into its forwardmost position, displacing finger 80 downwardly out of the way of its movement. When the leading edge of element 46b engages the forward wall of slot 16b, the trailing edge of element 46b clears finger 72 to enable it to return to its normal position illustrated in FIG. 10 to locate tip 78 in engagement against the trailing edge. Finger 72 cannot be cammed out of the way and thus prevents rearward movement of guard 30b to permanently lock guard 30b in its permanent protective position.

Referring now to the embodiment hereof illustrated in FIGS. 11-18, there is disclosed a scalpel wherein like reference numerals are applied to like parts as in the previous embodiments, followed by the suffix c. Thus, in FIGS. 11-13, there is illustrated a scalpel handle 12c having a blade 14c secured to the end of handle 12c and including a central slot 16c. In this form, slot 16c includes centrally disposed upper and lower ribs 90 and 92, respectively (see FIG. 18), defining tracks 94 and 96 along opposite sides thereof, respectively. A catch 99 comprised of a generally triangular ramp is disposed in the slot 16c along track 96 in a forward portion of slot 16c. Adjacent the opposite ends of slot 16c, there are provided fingers 98 and 100, respectively, which project into the slot and face in opposite directions. Fingers 98 and 100 are independently and resiliently movable away from their illustrated positions in slot 16c. The handle 12c includes the ribs 21c and 23c along the upper and lower edges of handle 12c, similarly as in the previous embodiment for purposes of gripping the scalpel, and also the rim 18c for engaging the margins of the side members 32c and 34c of the guard which will now be described.

Figure 17:
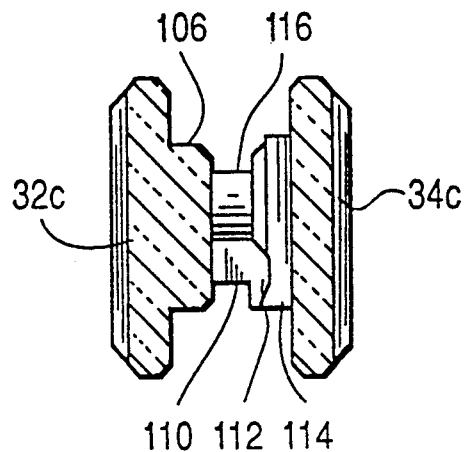
FIG. 17 is a cross-sectional view of the guard illustrated in FIG. 14 and taken generally about on line 17—17 in FIG. 14.
Figure 18:
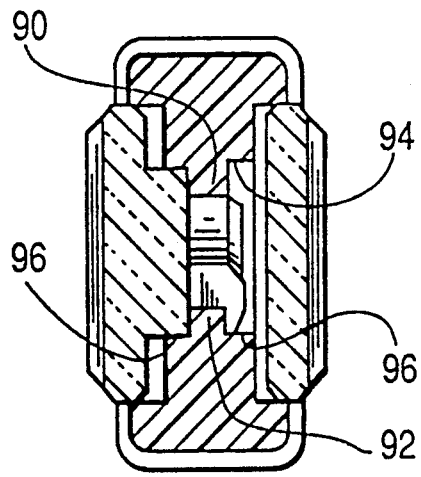
FIG. 18 is a cross-sectional view of the guard of the embodiment illustrated in FIGS. 11-17 taken generally about on line 18—18 in FIG. 11.

Referring particularly to FIGS. 14-17, the guard 30c is preferably integrally molded of one-piece and includes a pair of elongated side members 32c and 34c. The side members are secured along their forward ends and forward edges one to the other by a crosspiece 104 and are otherwise free of connection from one another. Adjacent the distal end of side member 32c is an inwardly extending boss 106 mounting an inwardly projecting cylindrical pin 108 and a latching detent 110 forwardly of pin 108. As best illustrated in FIG. 17, latching detent 110 has a downwardly turned tip 112. Side member 34c has a similar boss 114 located forwardly of boss 106. An inwardly extending cylindrical pin 116 and a pair of latching detents 118 and 120 project inwardly from boss 114. Latching detents 118 and 120 have downwardly formed tips, e.g., the tip 122 on latching detent 118, illustrated in FIG. 16.

To assembly the guard 30c and handle 12c one to the other, the side members 32c and 34c are spread apart at their distal ends such that the pin 108 and latching detent 110 are received in the slot 16c from one side of the handle, while the pin 116 and latching detents 118 and 120 are received in the slot from the opposite side of handles 16c. Because of the flexible nature of the latching detents, the tips of the detents snap past the lower rib 92 to engage on respective opposite sides thereof. Thus, the tip 112 of latching detent 110 maintains the distal end of side member 32c in close adjacency to the side of handle 12c, while the engagement of the tips of latching detents 118 and 120 along the opposite side of the central rib maintains the distal end of side member 34c adjacent the opposite side of handle 12c. Thus, the side members 32c and 34c are not directly connected to one another through slot 16c. Pins 108 and 116 bear along the upper and lower ribs 90 and 92, respectively. Consequently, the guard 30c is mounted for longitudinal sliding movement relative to the handle by the engagement of the edges of the guard side members with the rim 18c of the handle and the engagement of pins 108 and 116 in slot 16c, the tips of the latching detents maintaining the side members of the guard in close adjacency to the opposite sides of the handle, respectively.

Figure 11:
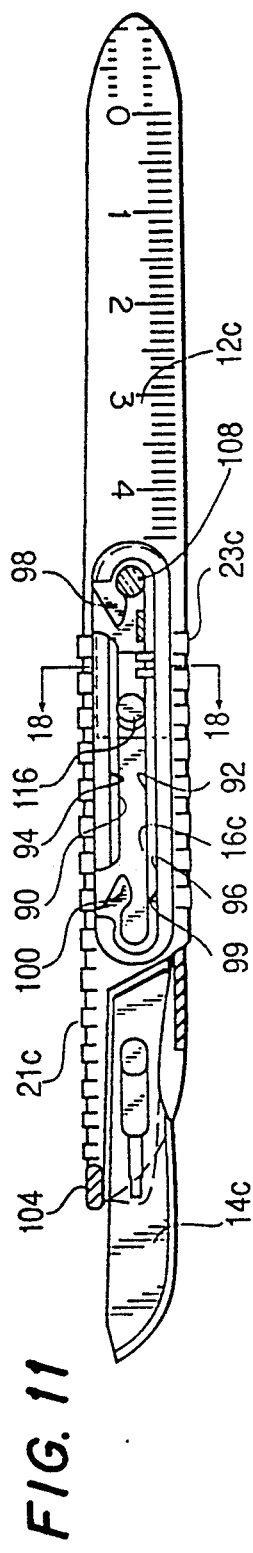
FIG. 11 is a side elevational view of a disposable scalpel with guard constructed in accordance with the present invention, with one side of the guard omitted, illustrating the internal connection between the other side of the guard and the scalpel handle with the guard in a retracted position.
Figure 12:
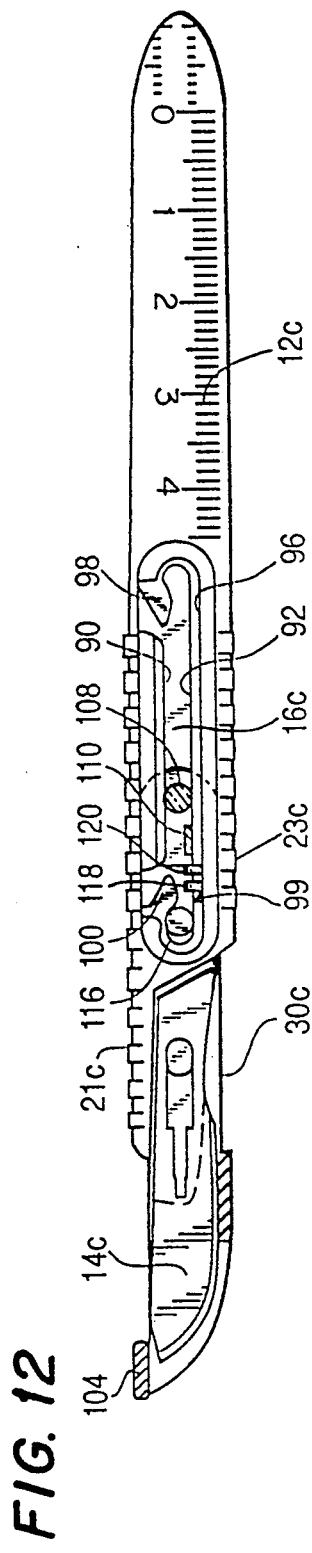
FIG. 12 is a side elevational view similar to FIG. 11, with the guard in a temporary protective position.
Figure 13:
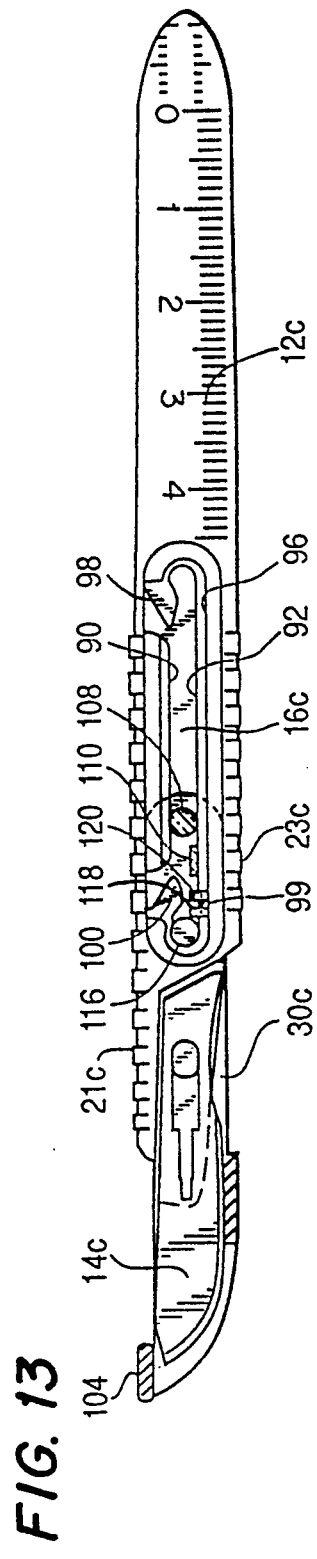
FIG. 13 is a view similar to FIG. 11, with the guard illustrated in a permanent protective position.
Figure 16:
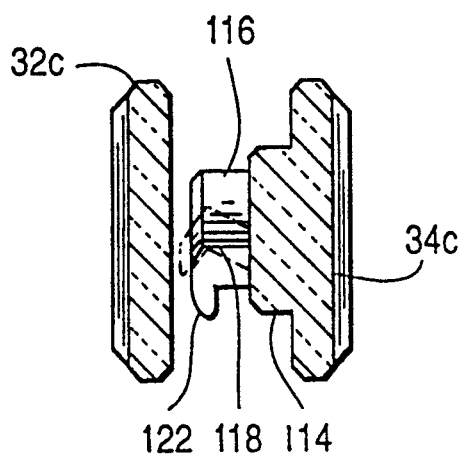
FIG. 16 is a cross-sectional view of the guard illustrated in FIG. 14 and taken about on line 16—16 in FIG. 14.

With the guard assembled to the handle as described above, the guard is movable between a retracted position exposing the blade 14c for use as illustrated in FIG. 11, a temporary protective position covering and overlying the blade 14c as illustrated in FIG. 12, and a permanent protective position overlying blade 14c as illustrated in FIG. 13. Thus, the guard may be retracted or displaced rearwardly along handle 12c such that the pin 108 is first biased out of the rearward path of movement of the pin and then returns to its predetermined position illustrated in FIG. 11, temporarily locking the pin 108 in the rearward end of slot 16c. In this position, the guard is retracted, exposing the blade for use. To temporarily cover the blade, as illustrated in FIG. 12, the guard is displaced forwardly relative to handle 12c, with the pins and latching detents sliding along the slot 16c. Pin 116 thus engages finger 100, moves it out of the way of further forward movement of pin 116 until it resiliently flexes back into the position illustrated in FIG. 12 to releasably prevent rearward movement of the guard relative to the handle. Simultaneously, the tip 122 of the first latching detent 118 engages the initial portions of the ramp of the triangularly-shaped catch 99 along track 96 to prevent the guard from moving further forwardly in slot 16c. Thus, the guard is temporarily locked in a protective position with its forward portion overlying blade 14c. Note also that the pins 108 and 116, not only serve as guides in slot 16c, but also constitute locking means for releasably retaining the guard in the temporary protective and retracted positions in cooperation with the two locking fingers 98 and 100, respectively. Locking finger member 100 in cooperation with pin 116 releasably locks the guard in the protective position and locking finger 98 in cooperation with pin 108 releasably maintains the guard in the retracted position.

To locate the guard in a permanent locking position permanently covering blade 14c, the guard is displaced forwardly from the position illustrated in FIG. 12 to the position illustrated in FIG. 13. In displacing the guard forwardly, tip 122 rides over the ramp of catch 99 such that the tips of the latching members 118 and 120 straddle or lie on opposite sides of the catch 99. Simultaneously, the pin 116 engages in the forward end of the slot. Thus, further movement of the guard forwardly is prevented by the engagement of the pin in the forward end of the slot and the engagement of the trailing tip of latching detent 120 along the ramp of catch 99. Rearward movement of guard 30c relative to handle 12c is prevented in this permanently locked position by the engagement of the tip 122 of the forward latching detent 118 against the flat or perpendicular side of catch 99. It will be appreciated that throughout the full range of sliding movement of the guard relative to the handle, the tips of the latching detents 110, 118 and 120 prevent the side members from spreading laterally outwardly from the handle.

In all of the embodiments hereof, it will be appreciated that the connection between the guard and handle provides a scalpel assembly of greater integrity and strength, i.e., stiffer, than either of the handle or guard individually. Also, the guard may be formed of a transparent or semi-transparent material. Thus, with appropriate identification markings on the blade, the type of blade can be identified by the user with the guard in its protective position overlying the blade and without the need to retract the guard. Alternatively, the guard may be opaque and have a window with or without a magnifying glass and through which window the type of blade may be identified. Various types of coated blades or edges, e.g., blades or edges coated with polymer materials, such as polytetrafluoroethylene, may be used and the invention hereof is not limited to any particular blade, coated or uncoated.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A surgical scalpel blade, comprising:
   an elongated scalpel handle comprising an upper and a lower edge, and a slot opening through and between opposite sides of the handle wherein at least one of said upper and lower edges is exposed so as to facilitate gripping the handle during use;
   a scalpel blade carried by said handle adjacent one end thereof;
   a guard movably mounted to said handle for sliding movement relative to said handle between a protective position covering said blade and a retracted position exposing said blade for use;
   said guard including side members located adjacent said opposite sides of said handle, said side members each having an inwardly extending flange which is positioned in said slot wherein said flanges are secured to one another so as to form an element, said element being movable along said slot in response to sliding movement of said guard relative to said handle between said protective and retracted positions;
   a locking member carried by said handle in said slot for engaging said element in said protective position of said guard relative to said handle for releasably maintaining said guard in said protective position thereof and movable to enable said guard to move from said protective position toward said retracted position; and
   means carried by said handle and cooperable with said element in the retracted position of said guard to releasably maintain said guard in said retracted position relative to said handle.

2. A surgical scalpel blade according to claim 1 wherein said maintaining means includes a detent carried by said handle and engageable with said element for releasably locking said guard in said retracted position relative to said handle.

3. A surgical scalpel blade according to claim 1 including means for biasing said locking member into engagement with said element in said protective position of said guard relative to said handle, said locking member being displaced against the bias of said biasing means in response to sliding movement of said element from said protective position toward said retracted position.

4. A surgical scalpel blade according to claim 1 wherein said maintaining means includes a portion of said locking member.

5. A surgical scalpel blade according to claim 3 wherein said maintaining means includes a portion of said locking member, said locking member portion being engageable against said element in said retracted position of said guard relative to said handle under the bias of said biasing means to maintain said guard in said retracted position relative to the handle.

6. A surgical scalpel blade according to claim 5 wherein said locking member portion comprises a detent for releasably locking said guard in said retracted position relative to said handle, said locking member engaging said element in said protective position of said guard relative to said handle along a portion of said locking member spaced from the portion thereof engaging said element in the retracted position of the guard relative to said handle.

7. A surgical scalpel blade according to claim 1 wherein said guard is movable in a first direction along said handle from said protective position toward and into said retracted position and in a second direction along said handle opposite said first direction from said retracted position toward and into said protective position and from said protective position into a permanent locking position with said guard covering said blade.

8. A surgical scalpel blade according to claim 7 wherein said locking member engages said element in said permanent locking position of said guard relative to said handle to maintain said guard in said permanent locking position.

9. A surgical scalpel blade according to claim 1 wherein said handle includes elongated top and bottom edges thereof, said side members of said guard comprising discrete side members unconnected one to the other along said top edge of said handle, leaving said top handle edge free for engagement by the finger of a user of the scalpel.

10. A surgical scalpel blade according to claim 1 wherein said handle includes elongated top and bottom edges thereof including predetermined areas for engagement by the fingers of a user of the scalpel, at least one of said top and bottom edges of said handle having said predetermined areas free for engagement by the user's fingers when said guard lies in both said protective and said retracted positions.

11. A surgical scalpel blade according to claim 1 wherein said guard includes a transparent portion on at least one of said side members overlying said blade in the protective position of said guard on said handle for viewing an identification on said blade.

12. A surgical scalpel blade, comprising:
an elongated scalpel handle comprising an upper and a lower edge, and a slot opening through and between opposite sides of the handle wherein at least one of said upper and lower edges is exposed so as to facilitate gripping the handle during use;
a scalpel blade carried by said handle adjacent one end thereof;
a guard carried by said handle for sliding movement relative to said handle in a first direction from a temporary protective position covering said blade into a retracted position exposing said blade for use and in a second direction opposite said first direction from said retracted position through said temporary protective position into a permanent protective position covering said blade;
said guard having an element disposed in said slot and movable therealong in response to sliding movement of said guard relative to said handle in said first and second directions;
a locking member carried by said handle in said slot for engaging and releasably detenting said element in said temporary protective position of said guard relative to said handle and movable to enable said guard to move in said first direction form said temporary protective position toward said retracted position and in said second direction into said temporary protective position;
said locking member being movable to engage said element in said permanent protective position of said guard to prevent movement of said guard relative to said handle in said first direction thereby to permanently lock said guard in said permanent protective position.

13. A surgical scalpel blade according to claim 12 including means for biasing said locking member into engagement with said element in said temporary protective position of said guard relative to said handle, said locking member being displaced against the bias of said biasing means in response to sliding movement of said element in said first direction from said temporary protective position toward said retracted position, said locking member being movable by said biasing means in response to movement of said guard into said permanent locking position to prevent said guard from moving in said second direction.

14. A surgical scalpel blade according to claim 13 wherein said locking member is biased into the path of movement of said element in said second direction when said guard lies in said permanent locking position.

15. A surgical scalpel blade according to claim 12 including means carried by said handle and engageable with said element for maintaining said guard in said retracted position, means carried by said handle and engageable with said element in said temporary protective position of said guard for preventing movement of said guard in said second direction from said temporary protective position toward said permanent protective position.

16. A surgical scalpel blade according to claim 15 wherein said preventing means includes a finger projecting into the path of movement of said element upon attempted movement of said guard in said second direction, and means for biasing said finger to project into said path of movement of said element such that said element may displace said finger from said path of movement of said element when said guard is moved in said second direction from said temporary protective position toward said permanent protective position.

17. A surgical scalpel blade according to claim 12 wherein said handle includes elongated top and bottom edges thereof, said side members of said guard comprising discrete side members unconnected one to the other along said top edge of said handle, leaving said top handle edge free for engagement by the finger of a user of the scalpel.

18. A surgical scalpel blade according to claim 17 wherein said element has a longitudinal extent sufficient in cooperation with margins of said handle defining said slot to substantially preclude pivotal movement of said guard relative to said handle about an axis normal to and passing through opposite sides of said handle.

19. A surgical scalpel blade according to claim 12 wherein said locking member includes a first surface engaging a first surface on said element when said guard lies in said temporary protective position to prevent movement of said guard in said first direction, said locking member including a second surface engaging a second surface on said element when said guard lies in said retracted position to prevent movement of said guard in said second direction.

20. A surgical scalpel blade according to claim 19 wherein said locking member includes a third surface engageable with a third surface on said locking element when said guard lies in said permanent protective position.

21. A surgical scalpel blade according to claim 12 wherein said locking member includes a first finger having a surface engaging a first surface on said element when said guard lies in said temporary protective position to prevent movement of said guard in said first direction, a second finger carried by said handle in said slot having a surface engaging a second surface on said element when said guard lies in said retracted position to prevent movement of said guard in said second direction and means for biasing said first and second fingers for movement into positions enabling the surfaces of said first and second fingers to engage said element.

22. A surgical scalpel blade according to claim 21 including a third finger carried by said handle in said slot and having a surface for engaging a third surface on said element when said guard lies in said temporary protective position to prevent movement of said guard in said second direction toward said permanent locking position, and means for biasing said third finger to project the surface of said third finger into said path of movement of said element, said element displacing said third finger from said path of movement of said element when said guard is moved in said second direction from said temporary protective position toward said permanent protective position.

23. A surgical scalpel blade, comprising:
an elongated scalpel handle having elongated top and bottom edges and guide surfaces;
a scalpel blade carried by said handle adjacent one end thereof;
a guard carried by said handle for sliding movement relative to said handle between a protective position covering said blade and a retracted position exposing said blade for use;

said guard having an element engageable with said guide surfaces of said handle and movable along said handle in response to sliding movement of said guard relative to said handle between said protective and retracted positions, said guard having discrete side members unconnected one to the other along at least one of said top and bottom edges of said handle, leaving said one edge free for engagement by a finger of a user of the scalpel;

a locking member carried by said handle for engaging said element in said protective position of said guard relative to said handle for releasably maintaining said guard in said protective position thereof and movable to enable said guard to move from said protective position toward said retracted position; and means carried by said handle and cooperable with said element in the retracted position of said guard to releasably maintain said guard in said retracted position.

24. A surgical scalpel blade according to claim 23 wherein said element and said guide surfaces on said handle are cooperable one with the other to substantially preclude pivotal movement of said guard relative to said handle about an axis normal to and passing through opposite sides of said handle.

25. A surgical scalpel blade according to claim 23 wherein said handle has opposite sides having recesses defined by marginal edges for engaging the edges of the side members of said guard to substantially preclude pivotal movement of said guard relative to said handle about an axis normal to and passing through opposite sides of said handle.

26. A surgical scalpel blade according to claim 23 wherein said guard includes a transparent portion on at least one of said side members overlying said blade in the protective position of said guard on said handle for viewing an identification on said blade.

27. A surgical scalpel blade, comprising:

an elongated scalpel handle comprising an upper and a lower edge, and a slot opening through and between opposite sides of the handle wherein at least one of said upper and lower edges is exposed so as to facilitate gripping the handle during use;

a scalpel blade carried by said handle adjacent one end thereof, a guard carried by said handle for sliding movement relative to said handle between a protective position covering said blade and a retracted position exposing said blade for use;

said guard including side members overlying said opposite sides of said handle, respectively, said guard carrying locking means disposed in said slot and movable along said slot in response to sliding movement of said guard relative to said handle;

a locking member carried by said handle in said slot for engaging said locking means in said protective position of said guard relative to said handle for releasably locking said guard in said protective position thereof and movable to enable said guard to move from said protective position toward said retracted position; and means carried by said handle and cooperable with said locking means in the retracted position of said guard to releasably maintain said guard in said retracted position relative to said handle.

28. A surgical scalpel blade according to claim 27 wherein said maintaining means includes a detent carried by said handle and engageable with said locking means for releasably locking said guard in said retracted position relative to said handle.

29. A surgical scalpel blade according to claim 27 including means for biasing said locking member into engagement with said locking means in said protective position of said guard relative to said handle, said locking member being displaceable against the bias of said biasing means in response to sliding movement of said guard from said protective position toward said retracted position.

30. A surgical scalpel blade according to claim 27 wherein said maintaining means includes a portion of said locking member.

31. A surgical scalpel blade according to claim 29 wherein said maintaining means includes a portion of said locking member, said locking member portion being engageable against said element in said retracted position of said guard relative to said handle under the bias of said biasing means to maintain said guard in said retracted position relative to the handle.

32. A surgical scalpel blade according to claim 27 wherein said guard is movable in a first direction along said handle from said protective position toward and into said retracted position and in a second direction along said handle opposite said first direction from said retracted position toward and into said protective position and from said protective position into a permanent locking position with said guard covering said blade.

33. A surgical scalpel blade according to claim 27 wherein said handle includes elongated top and bottom edges thereof, said side members of said guard comprising discrete side members unconnected one to the other along said top edge of said handle, leaving said top handle edge free for engagement by the finger of a user of the scalpel.

34. A surgical scalpel blade according to claim 27 wherein said handle has opposite sides having recesses defined by marginal edges for engaging the edges of the side members of said guard to substantially preclude pivotal movement of said guard passing through opposite sides of said handle.

35. A surgical scalpel blade according to claim 27 wherein said side members comprise inwardly extending latching detents which are positioned in said slot and engageable with said handle for preventing displacement of said side members laterally outwardly in a direction away from said handle.

36. A surgical scalpel according to claim 35 wherein said preventing means includes a rib on said handle in said slot and extending longitudinally thereof, and a projection carried by each side member and engageable along a side of said rib opposite from the side member carrying said projection whereby said projection engages said rib to prevent lateral outward movement of said member away from said handle.

37. A surgical scalpel handle according to claim 36 wherein each said projection is carried by said guard for sliding movement therewith relative to said handle upon movement of said guard relative to said handle between said protective and said retracted positions.

38. A surgical scalpel handle according to claim 37 wherein said locking means includes a pin carried by each side member and extending into said slot at longitudinally spaced positions therealong, said locking member being located for engaging one of said pins in said protective position of said guard relative to said handle, said maintaining means being located for engaging the other of said pins in said retracted position of said guard relative to said handle.

39. A surgical scalpel blade according to claim 38 wherein said side members comprise inwardly extending latching detents which are positioned in said slot and engageable with said handle for preventing displacement of said side members laterally outwardly in a direction away from said handle.

40. A surgical scalpel blade according to claim 27 wherein said guard is movable in a first direction along said handle form said protective position toward and into said retracted position and in a second direction along said handle opposite said first direction from said retracted position toward and into said protective position and from said protective position into a permanent locking position with said guard covering said blade, wherein said side members comprise inwardly extending latching detents which are positioned in said slot and are engageable with said handle for preventing displacement of said side members laterally outwardly in a direction away from said handle, a catch disposed along said slot, said displacement preventing means for one of said side members being engageable with said catch upon movement of said guard relative to said handle into said protective position to releasably prevent movement of said guard in said second direction from said protective position into said permanent locking position.

41. A surgical scalpel blade according to claim 40 wherein said engageable displacement preventing means is engageable with said catch upon movement of said guard relative to said handle into said permanent locking position to prevent movement of said guard in said first direction from said permanent locking position.

42. A surgical scalpel blade, comprising:
an elongated scalpel handle having a slot opening through and between opposite sides of the handle;
a scalpel blade carried by said handle adjacent one end thereof;
a guard carried by aid handle for a sliding movement relative to said handle between a protective position covering said blade and a retracted position exposing said blade for use;
said guard including side members overlying said opposite sides of said handle, respectively, each side member comprising at least one inwardly extending latching detent which is positioned in said slot for securing said member to said handle and at least one guide extending inwardly for guiding said guard and said handle relative to one another in response to sliding movement of said guard relative to said handle between said protective and retracted positions, said guides being disposed at longitudinally spaced positions relative to one another along said slot;
a pair of longitudinally spaced locking fingers carried by said handle in said slot for engaging said guides, respectively, in said protective and retracted positions of said guard relative to said handle, one of said locking fingers being engageable with one of said guides to releasably maintain said guard in said protective position thereof, the other of said locking fingers being engageable with the other of said guides to releasably maintain said guard in said retracted position relative to said handle; and
means extending into said slot from each of said side members and engageable with said handle for preventing displacement of said side members laterally outwardly in a direction away from said handle.

43. A surgical scalpel according to claim 42 wherein said preventing means includes a rib on said handle in said slot and extending longitudinally thereof, and a projection carried by each side member and engageable along a side of said rib opposite from the side member carrying said projection whereby said projection engages said rib to prevent lateral outward movement of the said member away from said handle.

44. A surgical scalpel handle according to claim 43 wherein each said projection is carried by said guard for sliding movement therewith relative to said handle upon movement of said guard relative to said handle between said protective and said retracted positions.

45. A surgical scalpel handle according to claim 42 wherein said guides include a pair of pins engageable along said rib.

46. A surgical scalpel handle according to claim 42 wherein said scalpel blade has an edge coated with a polymer material.

47. A surgical scalpel blade according to claim 1 wherein said slot on said handle is centrally located on said handle such that a sufficient portion of the handle remains substantially completely exposed with the guard int he retracted position so as to allow an operator to secure the handle in one hand while shifting the position of the guard with fingers of the same hand.

48. A surgical scalpel blade according to claim 1 wherein said handle further comprises a plurality of ribs longitudinally spaced one from the other along the upper edge of the handle, said ribs exposed in all positions of the guard so as to facilitate gripping the handle during use.

49. A surgical scalpel blade according to claim 12 wherein said slot on said handle is centrally located on said handle such that a sufficient portion of the handle remains substantially completely exposed with the guard in the retracted position so as to allow the operator to secure the handle in one hand while shifting the position of the guard with fingers of the same hand.

50. A surgical scalpel blade according to claim 12 wherein said handle further comprises a plurality of ribs longitudinally spaced one from the other along the upper edge of the handle, said ribs exposed in all positions of the guard so as to facilitate gripping the handle during use.

51. A surgical scalpel blade according to claim 27 wherein said slot on said handle is centrally located on said handle such that a sufficient portion of the handle remains substantially completely exposed with the guard in the retracted position so as to allow an operator to secure the handle in one hand while shifting the position of the guard with fingers of the same hand.

52. A surgical scalpel blade according to claim 42 wherein said slot on said handle is centrally located on said handle such that a sufficient portion of the handle remains substantially completely exposed with the guard int he retracted position so as to allow an operator to secure the handle in one hand while shifting the position of the guard with fingers of the same hand.

53. A surgical scalpel according to claim 42 wherein said guard is movable in a first direction along said handle from said protective position toward and into said retracted position and in a second direction along said handle opposite said first direction from said retracted position toward and into a protective position and from said protective position into a permanent locking position with said guard covering the blade.

54. A surgical scalpel according to claim 1 wherein at least one edge of said handle is completely exposed regardless of the position of the guard.

55. A surgical scalpel according to claim 12 wherein at least one edge of said handle is completely exposed regardless of the position of the guard.

56. A surgical scalpel according to claim 23 wherein at least one edge of said handle is completely exposed regardless of the position of the guard.

57. A surgical scalpel according to claim 27 wherein at least one edge of said handle is completely exposed regardless of the position of the guard.

58. A surgical scalpel according to claim 42 wherein at least one edge of said handle is completely exposed regardless of the position of the guard.

* * * * *